United States Patent
Vivien et al.

(10) Patent No.: US 10,675,409 B2
(45) Date of Patent: Jun. 9, 2020

(54) NEEDLELESS INJECTION DEVICE WITH AN IMPROVED SEALING GASKET

(71) Applicant: CROSSJECT, Dijon (FR)

(72) Inventors: Gilles Vivien, Malakof (FR); Xavier Vigot, Veronnes (FR)

(73) Assignee: CROSSJECT, Dijon (FR)

( * ) Notice: Subject to any disclaimer, the term of this patent is extended or adjusted under 35 U.S.C. 154(b) by 219 days.

(21) Appl. No.: 15/848,790

(22) Filed: Dec. 20, 2017

(65) Prior Publication Data
US 2018/0110924 A1 Apr. 26, 2018

Related U.S. Application Data

(63) Continuation of application No. PCT/FR2016/051658, filed on Jun. 30, 2016.

(30) Foreign Application Priority Data

Jun. 30, 2015 (FR) ..................................... 15 56161

(51) Int. Cl.
*A61M 5/20* (2006.01)
*A61M 5/30* (2006.01)
(Continued)

(52) U.S. Cl.
CPC ................ *A61M 5/20* (2013.01); *A61M 5/30* (2013.01); *A61M 5/3129* (2013.01); *F16L 17/04* (2013.01); *A61M 2005/3132* (2013.01)

(58) Field of Classification Search
CPC ........ A61M 5/20; A61M 5/30; A61M 5/3129; A61M 2005/3132
(Continued)

(56) References Cited

U.S. PATENT DOCUMENTS 5,833,243 A * 11/1998 Booker ................ F16J 15/3252
277/606
2003/0097093 A1* 5/2003 Navelier ................ A61M 5/30
604/68
(Continued)

FOREIGN PATENT DOCUMENTS

FR 2745619 9/1997
FR 2815544 4/2002
(Continued)

OTHER PUBLICATIONS

International Search Report for International Application PCT/FR2016/051658, dated Oct. 12, 2016.

*Primary Examiner* — Bhisma Mehta
*Assistant Examiner* — Nidah M Hussain
(74) *Attorney, Agent, or Firm* — Burris Law, PLLC

(57) ABSTRACT

The present disclosure is directed towards a needleless injection device including an injection system which includes at least one injection nozzle which delimits at least one injection channel, and which is axially delimited by an upper face arranged facing the lower face of the reservoir, and a lower face adapted to cooperate with a cap, and an upper sealing gasket which extends around the at least one channel and which is housed in an upper groove formed on the upper face of the nozzle, and the upper gasket has a wave-shaped radial section which comprises successively, along a radial direction, a recessed portion and a bump portion, said bump portion being adapted to be lying toward the recessed portion provided to this end, under the effect of the axial pressure exerted by the lower face of the reservoir on said sealing gasket.

10 Claims, 3 Drawing Sheets

(51) Int. Cl.
  *A61M 5/31* (2006.01)
  *F16L 17/04* (2006.01)
(58) Field of Classification Search
  USPC .......................................................... 604/68
  See application file for complete search history.

(56) References Cited

U.S. PATENT DOCUMENTS

| | | | | |
|---|---|---|---|---|
| 2004/0039367 A1* | 2/2004 | Alexandre | .......... | A61M 5/2046 |
| | | | | 604/500 |
| 2006/0189927 A1* | 8/2006 | Alexandre | .............. | A61J 1/062 |
| | | | | 604/72 |
| 2013/0317431 A1* | 11/2013 | KraMer | .................. | A61M 5/20 |
| | | | | 604/131 |

FOREIGN PATENT DOCUMENTS

| | | |
|---|---|---|
| FR | 2853837 | 10/2004 |
| FR | 2941027 | 7/2010 |

* cited by examiner

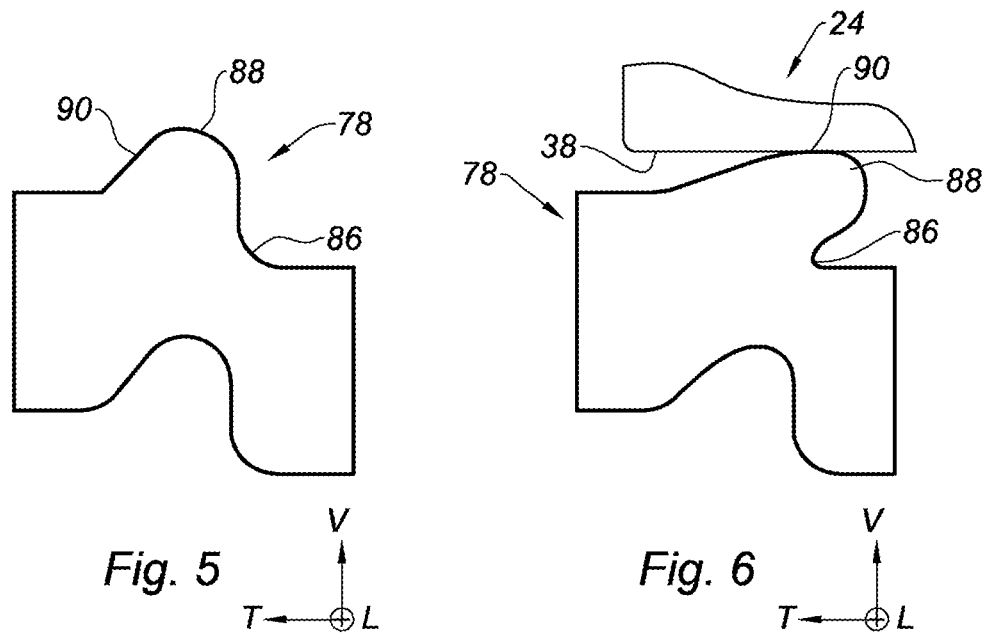
Fig. 5
Fig. 6
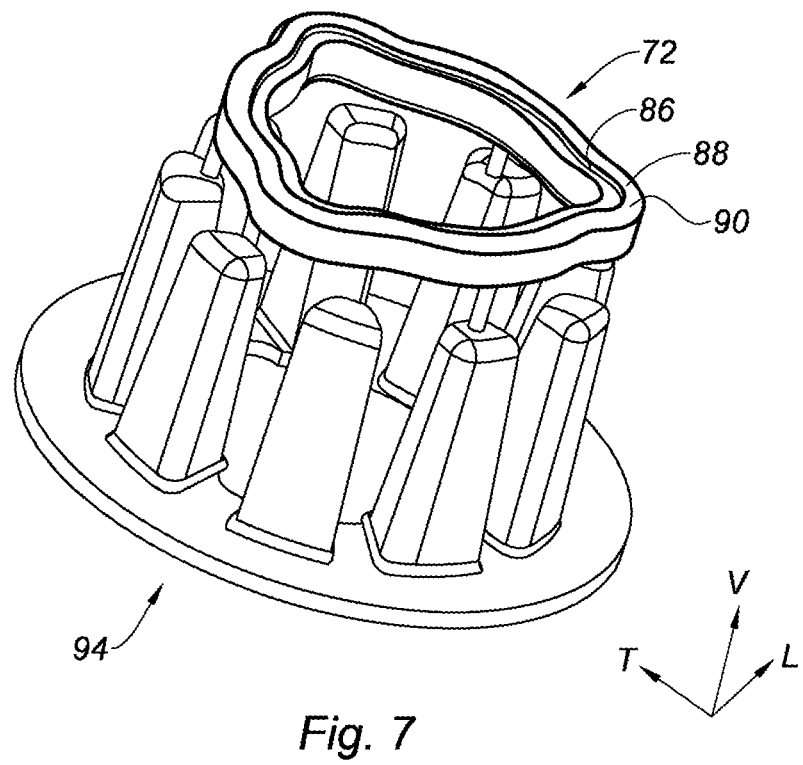
Fig. 7

NEEDLELESS INJECTION DEVICE WITH AN IMPROVED SEALING GASKET

CROSS-REFERENCE TO RELATED APPLICATIONS

This application is a continuation of International Application No. PCT/FR2016/051658, filed on Jun. 30, 2016, which claims the benefit of and priority to FR 15/56161 filed on Jun. 30, 2015. The disclosures of the above applications are incorporated herein by reference.

FIELD

The present disclosure relates to a needleless injection device.

BACKGROUND

The statements in this section merely provide background information related to the present disclosure and may not constitute prior art.

The technical field of the present disclosure is one of disposable pre-filled needleless injection devices, operating with an energy source such as a gas generator, and used for intradermal, subcutaneous and intramuscular injections, of a liquid active ingredient for a therapeutic use in human or veterinary medicine.

The active ingredient is constituted of a viscous liquid, a mixture of liquid, or a gel. The active ingredient may also be a solid dissolved in a solvent suitable for the injection or may be constituted of a pulverulent solid suspended at a certain concentration in a suitable liquid. The grain size distribution of the active ingredient is then be compatible with the diameter of the ducts in order to avoid obstructing them.

Generally, an injection device includes, for example as disclosed in patent application FR-A-2815544 (equivalent to WO 02/34317), a body comprising successively a gas generator, an expansion chamber, a reservoir containing the liquid active ingredient and an injection system.

The reservoir is constituted by a glass tube which is inserted into the body of the device and which is obstructed by an upstream plunger and a downstream plunger between which the liquid active ingredient is contained.

The downstream free end of the reservoir cooperates with an injection nozzle which delimits at least one injection channel extending axially along an injection axis.

The injection nozzle is axially delimited by an upper face bearing axially on the reservoir, and a lower face adapted to cooperate with a closure cap.

In addition, the injection device includes a hollow cover which envelops the body and which delimits a lower opening adapted for the passage of the injection nozzle.

In order to enable the injection of the active ingredient, the body is slidably mounted in the cover, from bottom to top along a sliding axis, between a rest position and an injection position, the driving of the body being carried out when the user presses the injection nozzle onto his skin.

The displacement of the body in the cover allows the gas generator to be triggered, generating a pressurized gas which drives in displacement the plungers in order to inject the active ingredient through the patient's skin via the injection nozzle.

In order to provide the sealing between the reservoir and the nozzle, in particular at the time of injection, an upper sealing gasket can be used.

The upper sealing gasket extends around the injection channels and is housed in an upper groove formed on the upper face of the nozzle. This gasket being designed to be axially compressed between the lower face of the reservoir and the upper face of the nozzle.

In a known manner, the gasket has a convex domed shape which is axially squashed by the reservoir.

It is observed that, when the gasket is compressed between the nozzle and the tube, the gasket may overflow from its groove and creep outwards between the nozzle and the reservoir, thereby creating a clearance conducive to the leakage of liquid.

In addition, this type of gasket generally forms lobes which bypass the injection channels of the nozzle, conferring a sinuous shape to the gasket, around the injection axis.

Such a sinuous shape may promote the apparition of pinches of the gasket when it is compressed by the reservoir, which may cause leakage between the nozzle and the reservoir.

SUMMARY

The present disclosure aims in particular at overcoming these and other drawbacks, and relates to a needleless injection device. In one form, the present disclosure includes an injection system which extends axially along an injection axis and which comprises at least, from upstream to downstream along the injection direction: at least one plunger; an active ingredient reservoir which has a lower face; an injection nozzle axially delimited by an upper face arranged facing the lower face of the reservoir; a lower face adapted to cooperate with a cap, the nozzle delimiting an injection channel extending axially from the upper face, to the lower face of the nozzle; an upper sealing gasket which extends around the at least one channel, and which is housed in an upper groove formed on the upper face of the nozzle. The gasket is designed to bear axially on the lower face of the reservoir. The upper gasket has a wave-shaped radial section which comprises successively, along a radial direction, a recessed portion and a bump portion, said bump portion being adapted to be lying toward the recessed portion provided to this end, under the effect of the axial pressure exerted by the lower face of the reservoir on said the sealing gasket.

In one form, the upper gasket according to the present disclosure improves the sealing of the nozzle, by lying and not by squashing, thereby inhibiting outward the pinching and the creeping of the gasket outwards.

In another form, the bump portion has an oblique flank which is arranged opposite the recessed portion and which forms a peripheral ramp adapted to allow the bump portion of the upper gasket to lie toward the recessed portion, under the effect of the axial pressure exerted by the reservoir on said the ramp of the upper gasket.

The ramp may promote the lying of the upper gasket, by cooperating with the lower face of the reservoir.

In another form, the recessed portion of the upper gasket is arranged radially toward the inside of the nozzle, and the bump portion of the upper gasket is arranged radially toward the outside of the nozzle, which allows the upper gasket to lie toward the center of the nozzle.

In addition, the recessed portion has a shape which is generally complementary to the shape of the bump portion of said upper gasket.

In one form, the injection channel is arranged in an offset manner relative to the injection axis, and the upper sealing gasket forms at least one lobe which bypasses said injection channel. Although the upper gasket has a tortuous shape, it provides sealing between the nozzle and the container when lying.

In another form, the injection nozzle delimits three injection channels which are angularly distributed in an even manner about the injection axis, and in that the upper gasket forms three lobes each bypassing one of said channels, so that the upper gasket has a generally circular shape which has three circle portions each forming a lobe.

According to yet another form, the upper gasket is made by overmolding on the nozzle, and the upper gasket is made of a thermoplastic elastomer adapted to chemically adhere on the nozzle made of polycarbonate.

In one form, the present disclosure includes an additional lower gasket which extends over the lower face of the nozzle, and which is adapted to provide the sealing with a closure cap of the nozzle, the lower gasket being integrally made with the upper gasket, said gaskets being linked to each other by at least one passage, provided to this end, formed in the nozzle.

According to another form, the active ingredient contained in the reservoir is selected from the group comprising the following active ingredients: Methotrezate, Adrenaline, Sumatriptan, Hydrocortisone, Naloxone, Midazolam, Apomorphine, Ethylnatrexone bromide Phytomenadione, Chlorpromazine hydrochloride, Zuclopenthixol acetate, Danaparoid sodium, Enoxaparin sodium, Estradiol cypionate, Medroxyprogesterone acetate, Medroparin calcium, Methylprednisolone acetate, Heparin calcium, Terbutaline.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 5 is a detail cross-sectional view, which illustrates a portion of the gasket of FIG. 2 at rest;

FIG. 6 is a detail cross-sectional view, which illustrates a portion of the gasket of FIG. 2 lying by the reservoir; and FIG. 7 is a perspective view which illustrates the gasket of FIG. 2 in its entirety.

Figure 1:
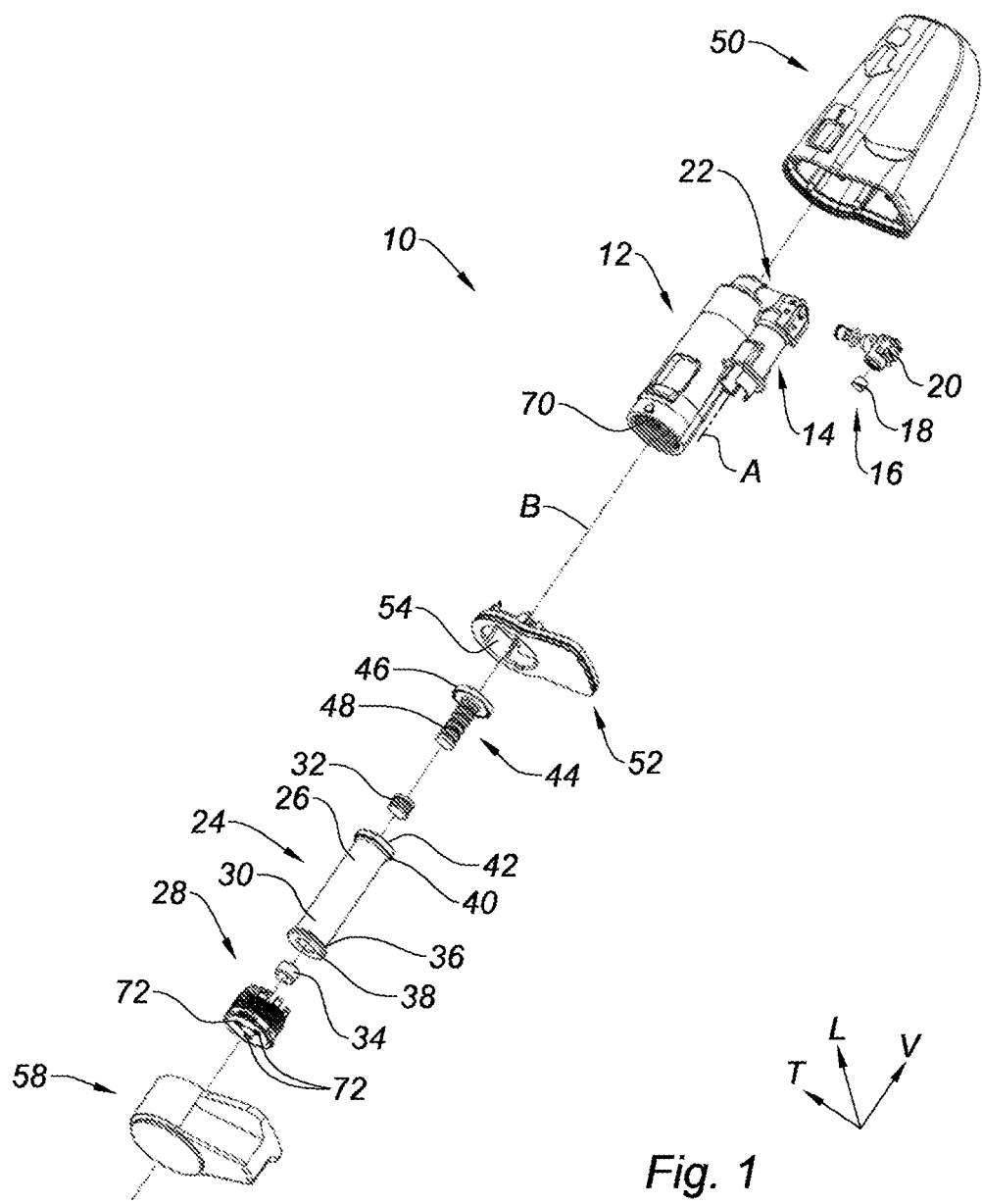
FIG. 1 is an axially exploded perspective view, which illustrates a needleless injection device, according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the following, the longitudinal, vertical, and transverse terminologies is adopted without limitation with reference to the trihedron L, V, T indicated in the figures.

In addition, in the present application, the terms "upper", "lower", "horizontal", "vertical", and their derivatives refer to the position or orientation of an element or a component, this position or orientation being considered with reference to the orientation of the device in the figures and to the trihedron L, V, T, without reference to the earth's gravity.

Similarly, the terms "axial" and "radial" should be understood with reference to the injection axis B of the injection device.

In all these figures, identical or similar reference numerals represent identical or similar members or sets of members.

FIG. 1 shows a needleless injection device 10, or needleless syringe, which includes a U-shaped body 12 comprising successively a percussion device 14, a gas generator 16 comprising a primer 18 and a pyrotechnic charge 20, an expansion chamber 22, a reservoir 24 containing the liquid active ingredient 26 and an injection nozzle 28.

The percussion device 14 and the gas generator 16 constitute a first linear subassembly of the body 12 which extends axially along a vertical sliding axis A, and the reservoir 24 containing the active ingredient 26 and the injection nozzle 28 form a second linear subassembly of the body 12 which extends axially along a second vertical injection axis B.

These two subassemblies are linked to one another by the expansion chamber 22 which has an axis perpendicular to the axes A, B of the subassemblies.

The reservoir 24 is constituted by a glass tube 30 obstructed by an upstream plunger 32 and a downstream plunger 34 between which the active ingredient 26 is contained, the plungers being made of an elastically-deformable elastomer-based material.

The reservoir 24 extends axially from a lower collar 36 which has an annular lower face 38 arranged opposite the injection nozzle 28, to an upper collar 40 having an annular upper face 42.

Also, according to FIG. 1, a cylindrical flexible diaphragm 44 includes an annular seat 46 which is axially interposed between the upper collar 40 of the reservoir 24 and the outlet orifice of the expansion chamber 22, and a cylindrical body 48 which extends axially inside the reservoir 24, above the upstream plunger 32.

The body 48 of the diaphragm 44 is designed to extend axially, under the effect of the pressure of the gas generated by the gas generator 16, in order to push the upstream plunger 32.

Referring to FIG. 1, the body 12 is enveloped by a hollow cover 50 which delimits a lower opening closed by a horizontal base 52 forming a cover bottom.

The base 52 delimits a circular passage 54 about the injection axis B which is adapted for the passage of the injection nozzle 28 and of the downstream end of the body 12, so that the nozzle 28 includes a lower section protruding vertically downwards out of the cover 50.

Also, the injection device 10 is equipped with a stopper 58 which is removably mounted on the body 12 by a bayonet-type locking means.

Figure 2:
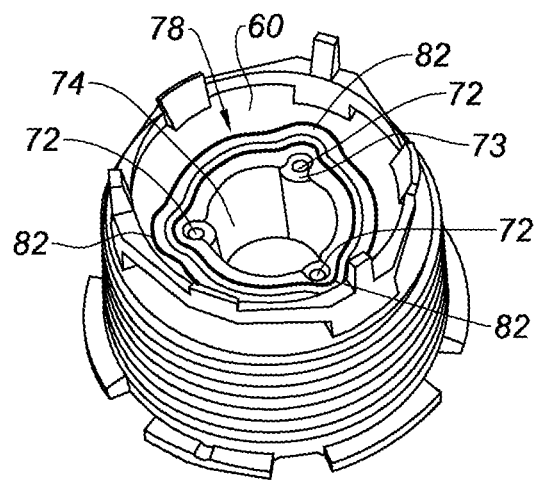
FIG. 2 is a top perspective view, which illustrates the nozzle of FIG. 1 equipped with an upper sealing gasket.
Figure 2:
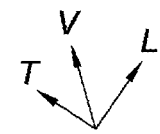
Figure 3:
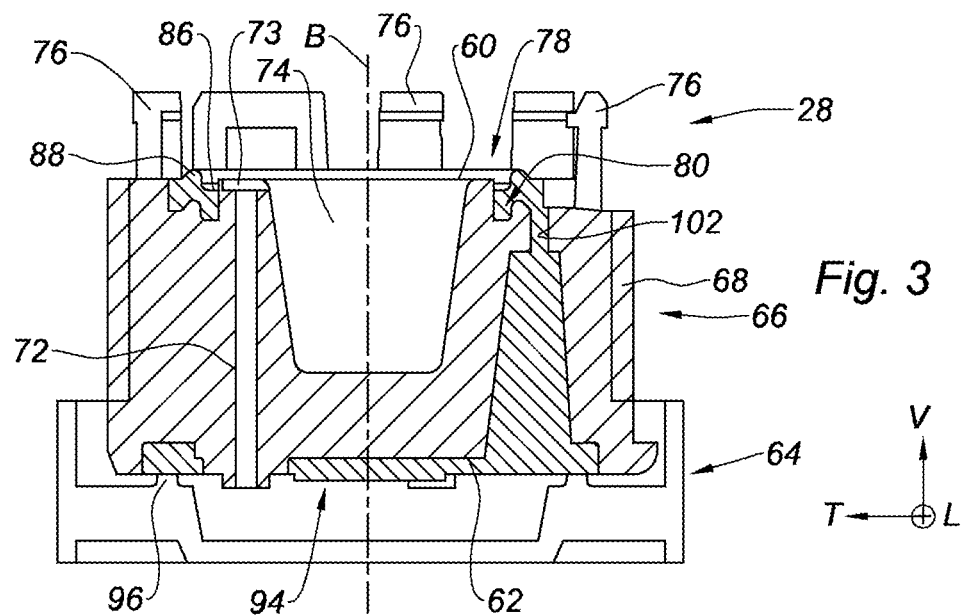
FIG. 3 is a schematic cross-sectional view, which illustrates the nozzle of FIG. 1 equipped with a sealing gasket.
Figure 3:
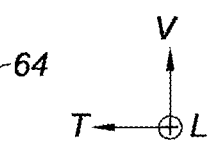

The injection nozzle 28, illustrated in FIGS. 2 and 3, has a generally cylindrical shape which extends axially along the injection axis B from an upper face 60 bearing axially on the lower face 38 of the reservoir 24, to an injection lower face 62 adapted to cooperate with a closure cap 64.

The cylindrical peripheral face 66 of the nozzle 28 has a thread 68 designed to screw the nozzle 28 on the free end of the body 12 equipped with a complementary tapping 70 shown in FIG. 1.

The nozzle 28 delimits three axial injection channels 72 which extend parallel to the injection axis B and which are angularly arranged in an even manner about the injection axis B, each channel 72 opening into the upper face 60 and into the lower face 62 of the nozzle 28.

The lower free end of each channel 72 forms a mouthpiece protruding axially from the lower face 62 of the nozzle 28.

In addition, the nozzle 28 delimits a central housing 74 which is adapted to receive the downstream plunger 34 subsequently to the triggering of the injection.

More particularly, the upper free end of each channel 72 forms a flaring 73 which communicates with the housing 74, to allow the active ingredient 26 to penetrate into each channel 72, from the housing 74.

Indeed, when the gas generator 16 is triggered, the pressurized gas pushes the liquid column formed by the upstream plunger 32, the active ingredient 26 and the downstream plunger 34, the downstream plunger 34 falling in the housing 74 of the nozzle 28 provided to this end to allow the active ingredient 26 to flow through the channels 72.

Also, the nozzle 28 is equipped with three hooks 76 which extend upwards from the upper face 60 of the nozzle 28 and which are adapted to cooperate with the lower collar 36 of the reservoir 24.

In order to provide the sealing between the nozzle 28 and the reservoir 24, the injection device 10 includes an upper sealing gasket 78 which extends about the injection axis B, and about the three channels 72, the upper gasket 78 being housed in a complementary upper groove 80 formed on the upper face 60 of the nozzle 28.

As shown in FIG. 2, the upper gasket 78 forms three lobes 82 each bypassing an associated channel 72, so that the upper gasket 78 has a generally circular shape which has three circle portions forming the lobes 82.

Referring to FIGS. 3 and 5, the upper gasket 78 has a wave-shaped radial section which comprises successively, along a transverse radial direction, a recessed portion 86 arranged radially toward the center of the nozzle 28, and a bump portion 88 arranged radially toward the outside of the nozzle 28.

The bump portion 88 is adapted to be lying toward the recessed portion 86 provided to this end, under the effect of the axial pressure exerted by the lower face 38 of the reservoir 24 on the upper gasket 78, as illustrated in FIG. 6.

To this end, the bump portion 88 of the upper gasket 78 has an oblique flank which is arranged opposite the recessed portion and which forms a peripheral ramp 90 adapted to allow the folding, or the lying, of the bump portion 88 toward the recessed portion 86, under the effect of the axial pressure exerted by the reservoir 24 on the ramp 90.

The ramp 90 extends from bottom to top, radially toward the center of the nozzle 28.

The term "lying", related to the bump portion 88 of the upper gasket 78, means herein that the bump portion 88 is inclined toward the recessed portion 86, unlike a gasket which squashes and creeps.

In addition, the recessed portion 86 has a shape which is generally complementary to the shape of the bump portion 88 of the upper gasket, forming a housing in which the bump portion 88 can lie, at least partially.

Figure 4:
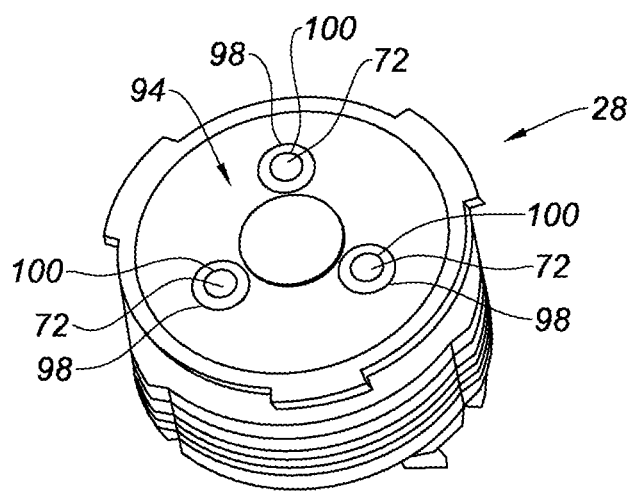
FIG. 4 is a bottom perspective view, which illustrates the lower face of the injection nozzle provided with a lower gasket.
Figure 4:
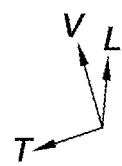

According to another aspect illustrated in FIGS. 4 and 7, the injection device 10 includes an additional lower gasket 94 which extends over the lower face 62 of the nozzle 28 and which is adapted to provide the sealing with the closure cap 64 of the nozzle 28.

For this purpose, as shown in FIG. 3, the lower gasket 94 is in the form of a radial planar disc which is adapted to bear axially on an axially protruding annular ridge 96 which is formed by the cap 64 and which extends about the injection axis B.

Also, the lower gasket 94 delimits three holes 98 for the passage of the mouthpieces 100 of each channel 72.

The lower gasket 94 and the upper gasket 78 are integrally made by overmolding on the nozzle 28, of a thermoplastic elastomer.

To this end, the nozzle 28 delimits three passages 102 (one of which is represented in FIG. 3) each linking the upper groove 80 formed on the upper face 60 of the nozzle 28 and the lower face 62 of the nozzle 28, in order to allow making the lower gasket 94 and the upper gasket 78 into one piece by overmolding on the nozzle 28.

Advantageously, the nozzle 28 is made by molding of polycarbonate and the elastomer used to make the upper gasket 78 and the lower gasket 94 is adapted to chemically adhere with the polycarbonate forming the nozzle 28.

According to one form, the upper gasket 78 and the lower gasket 94 are made of a thermoplastic elastomer with a 70 «Shore A» hardness, and a 650 percent elongation at break.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device including an injection system that extends axially along an injection axis and comprises at least, from upstream to downstream along the injection axis:
   at least one plunger;
   a reservoir that contains an active ingredient and has a lower face;
   an injection nozzle, axially delimited by an upper face arranged facing the lower face of the reservoir, and a lower face adapted to cooperate with a cap, the nozzle delimiting at least one injection channel extending axially from the upper face, to the lower face of the nozzle; and
   an upper sealing gasket that extends around the at least one channel, and housed in an upper groove formed on the upper face of the nozzle, the upper sealing gasket being configured to bear axially on the lower face of the reservoir;
   wherein the upper sealing gasket has a wave-shaped radial section that comprises successively, along a radial direction, a recessed portion and a bump portion, said bump portion being configured to be lying toward the recessed portion, under the effect of an axial pressure exerted by the lower face of the reservoir on the upper sealing gasket.

2. The needleless injection device according to claim 1, wherein the bump portion has an oblique flank arranged opposite the recessed portion and forms a peripheral ramp configured to allow the lying of the bump portion of the upper sealing gasket toward the recessed portion, under the effect of the axial pressure exerted by the reservoir on said ramp of the upper sealing gasket.

3. The needleless injection device according to claim 1, wherein the recessed portion of the upper sealing gasket is arranged radially toward an inside of the nozzle, and the bump portion of the upper gasket is arranged radially toward an outside of the nozzle.

4. The needleless injection device according to claim 1, wherein the recessed portion has a shape which is complementary to the shape of the bump portion of the upper sealing gasket.

5. The needleless injection device according to claim 1, wherein the at least one injection channel is arranged in an offset manner relative to the injection axis, and the upper sealing gasket forms at least one lobe which bypasses said at least one injection channel.

6. The needleless injection device according to claim 5, wherein the injection nozzle delimits three injection channels which are angularly distributed in an even manner about the injection axis, and in that the upper sealing gasket forms three lobes, each lobe bypassing one of said channels so that the upper sealing gasket has a circular shape which has three circle portions, each forming one lobe.

7. The needleless injection device according to claim 1, wherein the upper sealing gasket is made by overmolding on the nozzle.

8. The needleless injection device according to claim 1, wherein the upper sealing gasket is made of a thermoplastic elastomer adapted to chemically adhere on the nozzle, wherein the nozzle is made of polycarbonate.

9. The needleless injection device according to claim 1, further comprising a lower gasket which extends over the lower face of the nozzle, and which is adapted to provide sealing with a closure cap of the nozzle, the lower gasket being integrally made with the upper sealing gasket, wherein the lower gasket and the upper sealing gasket are linked to one another by at least one passage formed in the nozzle.

10. The needleless injection device according to claim 1, wherein the active ingredient contained in the reservoir is selected from the group consisting of:

Methotrexate, Adrenaline, Sumatriptan, Hydrocortisone, Naloxone, Midazolam, Apomorphine, Ethylnatrexone bromide, Phytomenadione, Chlorpromazine zydrochloride, Zuclopenthixol acetate, Danaparoid sodium, Enoxaparin sodium, Estradiol cypionate, Medroxyprogesterone acetate, Medroparin calcium, Methylprednisolone acetate, Heparin calcium, Terbutaline.

\* \* \* \* \*